United States Patent [19]

Harris

[11] Patent Number: 5,510,495
[45] Date of Patent: Apr. 23, 1996

[54] PROCESS FOR THE ISOLATION AND PURIFICATION OF ESTER FUNCTIONALIZED IMIDAZOLE INTERMEDIATES BY SELECTIVE HYDROLYSIS

[75] Inventor: Gregory D. Harris, Wilmington, Del.

[73] Assignee: The Du Pont Merck Pharmaceutical Company, Wilmington, Del.

[21] Appl. No.: 307,441

[22] Filed: Sep. 19, 1994

[51] Int. Cl.$^6$ .................... C07D 233/90; C07D 233/68
[52] U.S. Cl. .................................................. 548/334.5
[58] Field of Search ............................................ 548/334.5

[56] References Cited

U.S. PATENT DOCUMENTS 5,310,929  5/1994  Ardecky et al. .................. 548/253
5,312,828  5/1994  Finkelstein et al. .............. 514/381
5,338,740  8/1994  Carpino et al. .................. 514/259

OTHER PUBLICATIONS

Adams et al, "Organic Reactions", vol. II, Chapt. 9, pp. 376 to 404 (1944).
Starks et al, "Phase Transfer Catalysts", Chapt. 9, pp. 337 to 343 (1978).

Primary Examiner—Floyd D. Higel

[57] ABSTRACT

A method for isolating and purifying an ester functionalized imidazole compound, useful as an angiotensin (II) antagonist or as a key intermediate therefor, from a mixture of it with its regioisomer in a solvent, by treatment with an alkali metal hydroxide to achieve the regioselective hydrolysis of the undesired regioisomeric ester.

9 Claims, No Drawings

PROCESS FOR THE ISOLATION AND PURIFICATION OF ESTER FUNCTIONALIZED IMIDAZOLE INTERMEDIATES BY SELECTIVE HYDROLYSIS

FIELD OF THE INVENTION

This invention relates to a method for the isolation and purification of imidazole compounds useful as angiotensin II receptor inhibitor compounds or as key intermediates therefor. These methods involve the regioselective hydrolysis of ester functionalized imidazoles.

BACKGROUND OF THE INVENTION

Regioselective alkylation of polysubstituted imidazoles is of importance especially with regard to Angiotensin II antagonists. The mechanisms of selective alkylation are somewhat understood and can be used in some circumstances to control reaction products, i.e. the distribution of N-alkylated regioisomeric products. However, no generally applicable methods currently exist for the regloselective alkylation of these important imidazoles in quantitative yield. The product of the prior art is usually a mixture of regioisomers as shown in Scheme 1.

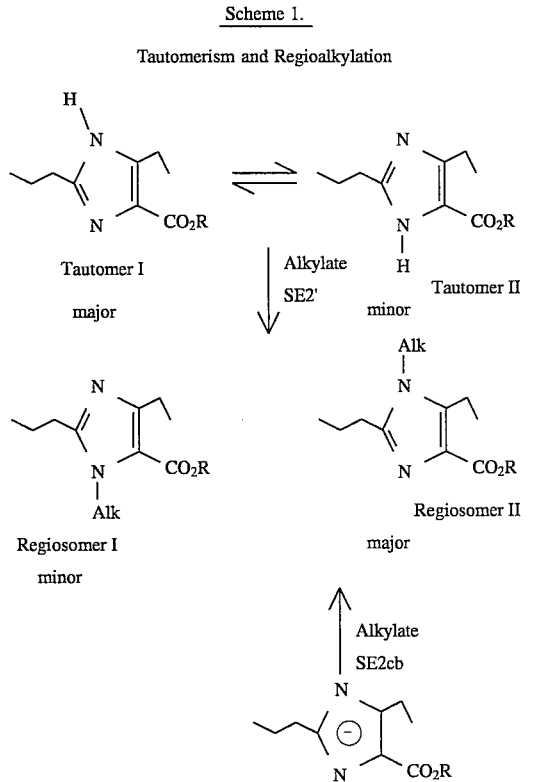

Japanese patent JP 4120063 A, Ishihara Sangyo Kaisha Ltd., describes the separation of 2-cyanoimidazole-sulphonamide derivatives by selectively hydrolyzing one of two imidazole compounds in the presence of an acid catalyst as shown in Scheme 2. This reference does not teach the selective hydrolysis of a carbon attached ester functional group.

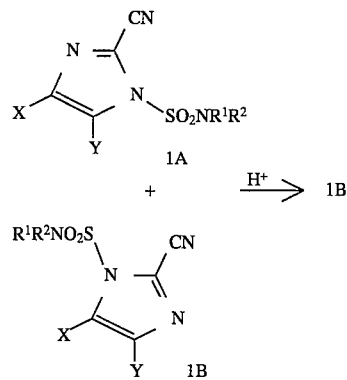

No references are known that teach the regioselective hydrolysis of ester functionalized N-alkylated imidazoles.

It is apparent, as determined by the nonquantitative formation of either regioisomer during N-alkylation, and the lack of suitable methods for the large scale purification of N-alkylated imidazole that a method of purifying these very important compounds to obtain pure products from alkylation is needed.

SUMMARY OF THE INVENTION

This invention relates to methods for the isolation and purification of ester functionalized N-alkylated substituted imidazoles of formula (I) from a mixture of compounds of formula (I) and formula (II)

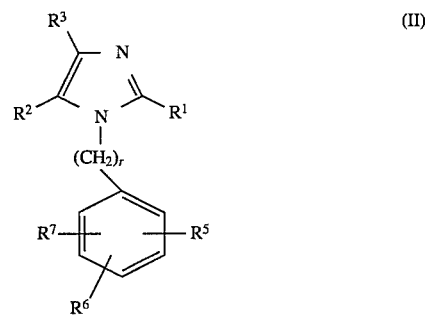

wherein:

$R^1$ is selected from H; C1–C6 alkyl, C1–C6 fluoroalkyl, C2–C10 alkenyl, or C2–C10 alkynyl each optionally substituted by —$CO_2$-(C1–C6 alkyl); C4–C10 cycloalkylalkyl, C3–C6 cycloalkyl, C5–C10 cycloalkylalkenyl, or C5–C10 cycloalkylalkynyl each optionally substituted by 1–13 —F or 1–3 —$CO_2$-(C1–C6 alkyl); phenyl, naphthyl, or aryl-(C1–C4 alkyl) optionally substituted with —F or —$CO_2$-

(C1–C6 alkyl); —(CH$_2$)$_s$O(CH$_2$)$_m$R5 optionally substituted with —F or —CO$_2$-(C1–C6 alkyl); benzyl optionally substituted with up to 2 groups selected from halo, C1–C4 alkoxy, NO$_2$, or C1–C4 alkyl;

R$^2$ is C$_1$–C$_6$ alkyl, C$_2$–C$_6$ alkenyl, C$_2$–C$_6$ alkynyl, phenyl-(C$_1$–C$_6$) alkyl, phenyl-(C$_1$–C$_6$) alkenyl, (C$_1$–C$_6$)alkoxy-(C$_1$–C$_6$)alkyl, hydroxy-(C$_1$–C$_6$)alkyl, hydroxy-(C$_2$–C$_6$)alkenyl, hydroxy-(C$_2$–C$_6$) alkynyl, aminocarbonylalkyl, carbonylaminoalkyl, halogen;

R$^3$ is —CN; —CONHR$^1$; or —CO$_2$R$^1$ where R$^1$ as defined above may not be H;

R$^5$ is H, Br, I, F, CF$_3$, (C$_1$–C$_4$) alkyl, —C(CF$_3$)$_2$OH, —NHSO$_2$CH$_3$, —C(=O)NHNHSO$_2$CF$_3$,

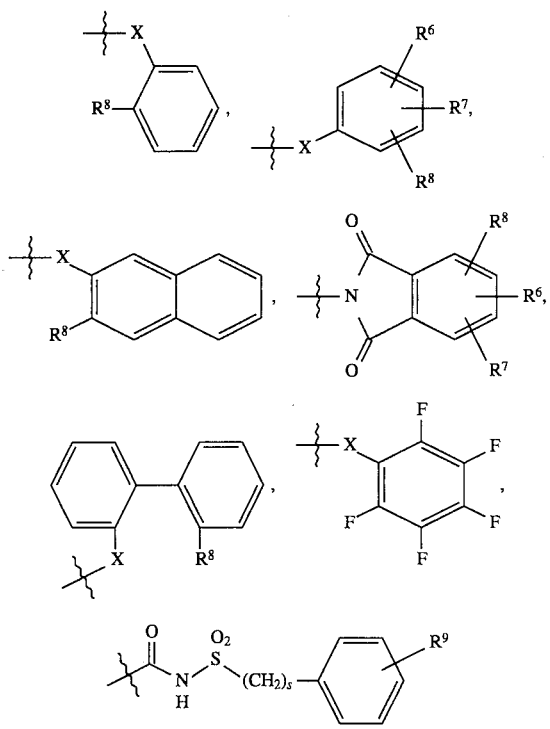

or aryl optionally substituted by R$^9$;

R$^6$ is H, halo, NO$_2$, C$_1$–C$_4$ alkyl, C$_1$–C$_4$ alkoxy, —NHSO$_2$CH$_3$, —NHSO$_2$CF$_3$, —CONHO-(C$_1$–C$_4$)alkyl, tetrazolyl, trityl protected tetrazolyl, or furyl;

R$^7$ is H, halo, C$_1$–C$_4$ alkyl, or C$_1$–C$_4$ alkoxy;

X is a single bond, —CO—, —CH$_2$—, —O—, —CONH—, —NHCO—, —OCH$_2$—, —CH$_2$O—, —NHSO$_2$—, —SO$_2$NH—, —CH=CH—, —CF=CH—, —CH=CF—, —CF=CF—, —CH$_2$CH$_2$—, —CF$_2$CF$_2$—, or

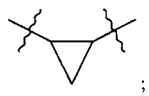;

R$^8$ is H, —NHSO$_2$CH$_3$, —NHSO$_2$CF$_3$, —NHCOCF$_3$, or —CONHNHSO$_2$CF$_3$;

R$^9$ is H, C1–C4 alkyl, or phenyl;

r is 0 to 2;
m is 1 to 5;
s is 0 to 5;
said method comprising the steps of:

contacting a mixture of compound of the formula (I) and its regioisomer of the formula (II) in a solvent system, which is:

a) a solvent or mixture of solvents, selected from a halogenated solvent, an ether solvent, a hydrocarbon solvent, a protic solvent, or an aprotic solvent, said solvent or mixture of solvents forming a single liquid phase; or b) a solvent mixture of at least two immiscible solvents, selected from the solvent groups defined in a) above, that results in more than one liquid phase, said solvent mixture additionally containing a phase transfer catalyst present in the range of 1–20% mole based upon the mixture of compounds of formula (I) and formula (II);

with 1–20 molar equivalents of an alkali metal hydroxide, and heating the mixture to solvent reflux for a period of time sufficient to preferentially hydrolyze the compound of formula (II) and separating the compound of formula (I) from the hydrolyzed products of compounds of formula (I) and formula (II).

The present invention may be generally understood according to Scheme 3.

Scheme 3.

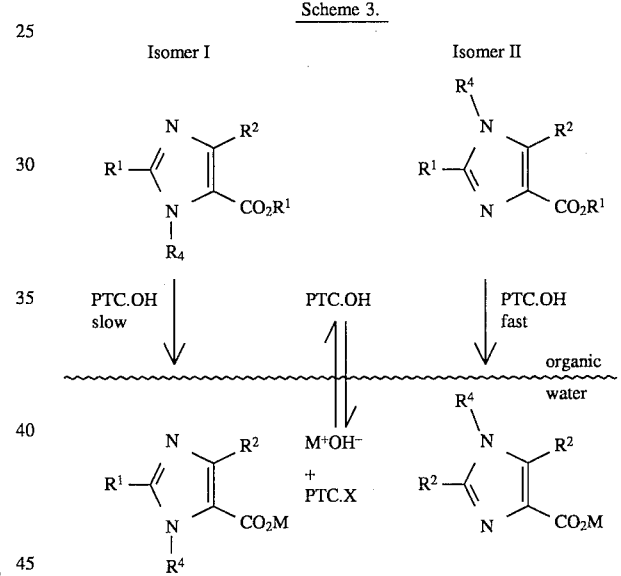

PTC = phase transfer catalyst;
M = alkali metal cation

DETAILED DESCRIPTION OF THE INVENTION

This invention provides a novel method for the isolation and purification of compounds of formula (I) from a mixture of compounds of formula (I) and formula (II) which are useful as Angiotensin II antagonists or as intermediates for the preparation therefor. In the present invention, an ester functionalized N-alkylated imidazole of formula (I) is obtained in the regioisomerically pure form from a mixture of N-alkylated free base regioisomers of formula (I) and formula (II).

The regioselective hydrolysis of ester functionalized N-alkylated imidazoles is made possible by the differences in the steric environment and/or electron density around the ester groups. These changes are caused by the proximity of the N-alkyl group as well as by the change in the electron character of the alkylated versus unalkylated nitrogen.

In this process, a mixture of regioisomeric compounds of formula (I) and formula (II) are treated with a strong base to more rapidly hydrolyze the ester of the compound of formula (II) over that of the compound of formula (I). The mixture of regioisomeric compounds of formulae (I) and (II), (mole ratio 75–99: 25–1; I:II), in a solvent system which is a) a solvent or mixture of solvents, selected from a halogenated solvent, an ether solvent, a hydrocarbon solvent, a protic solvent, or an aprotic solvent, said solvent or mixture of solvents forming a single liquid phase; or b) a solvent mixture of at least two immiscible solvents, selected from the above solvent groups, that results in more than one liquid phase, said solvent mixture additionally containing a phase transfer catalyst present in the range of 1–20% mole based upon the mixture of compounds of formula (I) and formula (II);

is contacted with 1–20 molar equivalents of an alkali metal hydroxide, and the mixture is heated to solvent reflux for a period of 10 min to 10 hrs so as to enrich the regioisomeric mixture of compounds of formulae (I) and (II) to the extent that they are present in a 95–100:5–0 (I:II) mole ratio. The compound of the formula (I) is then separated from the hydrolyzed products of compounds of the formulae (I) and (II).

The reaction of the present invention is carried out in suitable solvents which may be readily selected by one skilled in the art of organic synthesis, said suitable solvents generally being any solvent which is substantially nonreactive with the starting materials (reactants), the intermediates, or products at the temperatures at which the reactions are carried out, i.e., temperatures which may range from the solvent's freezing temperature to the solvent's boiling temperature. A given reaction may be carried out in one solvent or a mixture of more than one solvent. Depending on the particular reaction step, a suitable solvents for the reaction step may be selected.

The suitable solvents for this reaction include: a solvent, a mixture of solvents that results in one liquid phase, a mixture of solvents that results in more than one liquid phase. It is understood that when the suitable solvent is comprised of more than one liquid phase, i.e. biphasic, triphasic or more, the compound of formula (I) should be preferentially soluble in a phase other than the phase in which the hydrolyzed products of compounds of formula (I) and (II) are preferentially soluble in. Solvents of the present invention may be selected from: halogenated solvents, ether solvents, hydrocarbon solvents, protic solvents, and aprotic solvents.

Suitable halogenated solvents include, by way of example and without limitation: carbon tetrachloride, bromodichloromethane, dibromochloromethane, bromoform, chloroform, bromochloromethane, dibromomethane, butyl chloride, dichloromethane, tetrachloroethylene, trichloroethylene, 1,1,1-trichloroethane, 1,1,2-trichloroethane, 1,1-dichloroethane, hexafluorobenzene, 1,2,4-trichlorobenzene, o-dichlorobenzene, or fluorobenzene.

Suitable ether solvents include, by way of example and without limitation: dimethoxymethane, tetrahydrofuran, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, or t-butyl methyl ether.

Suitable hydrocarbon solvents include, by way of example and without limitation: benzene, cyclohexane, pentane, hexane, toluene, cycloheptane, methylcyclohexane, heptane, ethylbenzene, m-, o-, or p-xylene, octane, indane, nonane, or naphthalene.

Suitable protic solvents include, by way of example and without limitation: water, methanol, ethanol, 2-nitroethanol, 2-fluoroethanol, 2,2,2-trifluoroethanol, ethylene glycol, 1-propanol, 2-propanol, 2-methoxyethanol, 1-butanol, 2-butanol, i-butyl alcohol, t-butyl alcohol, 2-ethoxyethanol, diethylene glycol, 1-, 2-, or 3-pentanol, neo-pentyl alcohol, t-pentyl alcohol, diethylene glycol monomethyl ether, diethylene glycol monoethyl ether, cyclohexanol, anisole, benzyl alcohol, phenol, or glycerol.

Suitable aprotic solvents include, by way of example and without limitation: dimethylformamide (DMF), dimethylacetamide (DMAC), 1,3-dimethyl-3,4,5,6-tetrahydro- 2(1H)-pyrimidinone (DMPU), 1,3-dimethyl-2-imidazolidinone (DMI), N-methylpyrrolidinone (NMP), formamide, N-methylacetamide, N-methylformamide, acetonitrile, dimethyl sulfoxide, propionitrile, hexachloroacetone, acetone, ethyl methyl ketone, sulfolane, N,N-dimethylpropionamide, tetramethylurea, nitromethane, nitrobenzene, or hexamethylphosphoramide.

The preferred reaction solvent system for the method of the invention is a mixture of solvents which results in two liquid phases. The preferred solvent mixture is comprised of a water immiscible solvent and water.

Preferred water immiscible solvents include methylene chloride, t-butylmethyl ether, benzene, xylene, toluene, diethyl ether, or hexane.

As used herein, "alkali metal hydroxide" is intended to include by way of example and without limitation: sodium hydroxide, lithium hydroxide, potassium hydroxide or cesium hydroxide.

The preferred alkali metal hydroxide for the method of the invention for hydrolysis of compound (II) is sodium hydroxide or potassium hydroxide.

The preferred molar equivalent of the alkali metal hydroxide is 10–14.

As used herein, "phase transfer catalyst" is intended to mean any compound which would, in a biphasic or triphasic solvent system, enhance the solubility of the hydroxide ion in a phase in which it is not preferentially soluble, i.e. enhance the solubility of the hydroxide ion in the organic phase when the reaction solvent system is biphasic and comprised of water and a water immiscible organic solvent. A phase transfer catalyst may include, by way of example and without limitation, a quaternary ammonium salt such as tetrabutylammonium bromide; a crown ether such as 15-crown-5, 18-crown-6 or dicyclohexano-18-crown-6; or a phosphonium salt such as hexadecyltributylphosphonium bromide. It is understood that the counterion of the phase transfer catalyst may be replaced with others known to the skilled artisan: halide or hydroxide. It is further understood that the respective alkyl groups of the quaternary ammonium salt and phosphonium salt may also be replaced by with others known to those skilled in the art: C1–C16 alkyl, C3–C16 branched or cycloalkyl.

The preferred phase transfer catalyst for the method of the invention is a quaternary ammonium halide or hydroxide.

The preferred molar equivalents of phase transfer catalyst is 10–14% mole.

The compounds herein described may have asymmetric centers. All chiral, diastereomeric, and racemic forms are included in the present invention. Many geometric isomers of olefins, C=N double bonds, and the like can also be present in the compounds described herein, and all such stable isomers are contemplated in the present invention. It will be appreciated that certain compounds of the present invention contain an asymmetrically substituted carbon atom, and may be isolated in optically active or racemic forms. It is well known in the art how to prepare optically active forms, such as by resolution of racemic forms or by synthesis, from optically active starting materials. Also, it is realized that cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomer form is specifically indicated.

When any variable (for example, $R^1$, $R^2$, $R^3$, R5, m, etc.) occurs more than one time in any constituent or formula for a compound, its definition on each occurrence is independent of its definition at every other occurrence. Thus, for example, if a group is shown to be substituted with 0–3 $R^6$, then said group may optionally be substituted with up to three $R^6$ and $R^6$ at each occurrence is selected independently from the defined list of possible $R^6$. Also, combinations of substituents and/or variables are permissible only if such combinations result in stable compounds. By stable compound or stable structure it is meant herein a compound that is sufficiently robust to survive isolation to a useful degree of purity from a reaction mixture. Similarly, by way of example, for the group —$C(R^6)_2$—, each of the two $R^6$ substituents on C is independently selected from the defined list possible for $R^6$.

As used herein, "alkyl" is intended to include both branched and straight-chain saturated aliphatic hydrocarbon groups having the specified number of carbon atoms; "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono- or bicyclic ring systems, such as cyclopropyl, cyclobutyl, cyclopentyl, cyclohexyl, or cycloheptyl. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon—carbon bonds which may occur in any stable point along the chain, such as ethynyl, propynyl and the like.

"$C_4$–$C_{10}$ cycloalkylalkyl" is intended to mean a cycloalkyl group attached through an alkyl bridge. In a similar manner the term "C5–C10 cycloalkylalkenyl" is intended to mean a cycloalkyl group attached through an alkenyl brige, and the term "C5–C10 cycloalkylalkynyl" is intended to mean a cycloalkyl group attached through an alkynyl bridge.

As used herein, "fluoroalkyl" is intended to mean a C1–C6 straight chained or branched "alkyl" group substituted with 1 to 13 fluoro groups.

As used herein, "hydroxyalkyl" is intended to mean a $C_1$–$C_6$ straight chained or branched "alkyl" group substituted with 1 to 6 hydroxy groups.

"Halo" or "halogen" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; the term "arylalkyl" represents an aryl group attached through an alkyl bridge. By way of examples: the term "$C_7$–$C_{10}$ arylalkyl" is intended to refer to an aryl group attached through a $C_1$–$C_4$ alkyl bridge to the residue of the indicated compound; the term "($C_1$–$C_3$ alkyl)aryl" is intended to refer to a $C_1$–$C_3$ alkyl group which is attached through an aryl ring to the residue of the indicated compound; the term "aryl ($C_1$–$C_3$ alkyl)" is intended to refer to an aryl group attached through a $C_1$–$C_3$ alkyl group to the residue of the indicated compound.

When a bond to a substituent is shown to cross the bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. For example, when the substituent is phenyl, benzyl, or tetrazolyl, unless specified otherwise, said phenyl, benzyl or tetrazolyl group may be bonded to the rest of the compound of a given formula via any atom in such phenyl, benzyl, or tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogens on the designated atom is replaced with a selection from the indicated group, provided that the designated atom's normal valency is not exceeded, and that the substitution results in a stable compound.

The present invention may be better understood according to scheme 4.

Scheme 4.

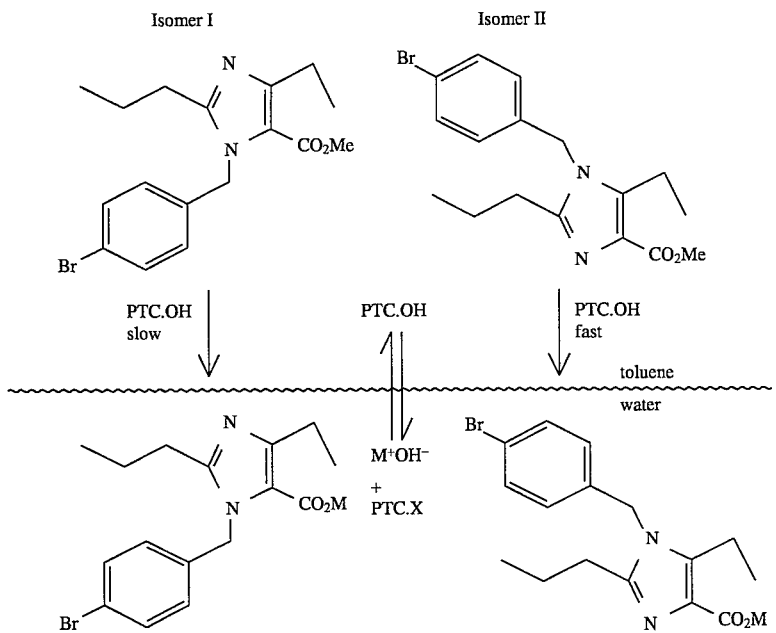

PTC = phase transfer catalyst;
M = alkali metal cation

The scope of the present invention may be further understood, without limitation, by the following example.

EXAMPLE 1

N-(4-bromobenzyl)-2-propyl-4-ethyl-5-carboxymethylimidazole 2-propyl-4-ethyl-5-carboxymethyl-imidazole (4 g; 0.02 moles) was dissolved in N,N dimethylacetamide (26 mL) under an atmosphere of nitrogen. 4-Bromobenzylbromide (5.08g; 0.021 moles) and anhydrous cesium carbonate (9.3 g; 0.029 moles) were added and the resulting mixture was stirred at 20° C. for 4 hours yielding an 80:20 (I:II) stereoisomeric mixture. Water (100 mL) and toluene (100 mL) were added. The mixture was agitated, allowed to settle and separated. Aqueous sodium hydroxide solution (10 Molar; 30 mL) and tetrabutyl ammomium bromide (1 g) were added and the resulting mixture refluxed with good agitation for 2 hours. The reaction mixture was cooled to 20° C. and separated. The organic phase was washed with water (30 mL) and then evaporated under reduced pressure to yield N-(4bromobenzyl)-2-propyl-4-ethyl-5-carboxymethyl imidazole as a clear oil (4.2 g; 56% yield).

EXAMPLE 2

N-[4-(O-(trityltetrazole)phenyl)benzyl]-4-ethyl-5-carboxymethyl-2-propyl-imidazole To a mixture of N-[4-(O-(trityltetrazole) phenyl)benzyl]-4-ethyl-5-carboxymethyl 2-propyl-imidazole and N-[4-(O-(trityltetrazole) phenyl)benzyl]-5-ethyl-4-carboxymethyl-2-propyl-imidazole (0.15 moles, 80:20 (I:II)) under an atmosphere of nitrogen was added aqueous sodium hydroxide solution (10 Molar; 30 mL), tetra-butyl ammomium bromide (1 g), and toluene (100 mL). The resulting mixture was refluxed with good agitation for 2 hours. The reaction mixture was cooled to 20° C. and separated. The organic phase was washed with water (30 mL) and then evaporated under reduced pressure to yield N-[4-(O-(trityltetrazole)phenyl)benzyl]-4-ethyl- 5-carboxymethyl-2-propyl-imidazole.

What is claimed is:

1. A method for the isolation and purification of a compound of the formula (I) from a mixture of compounds of the formula (I) and (II)

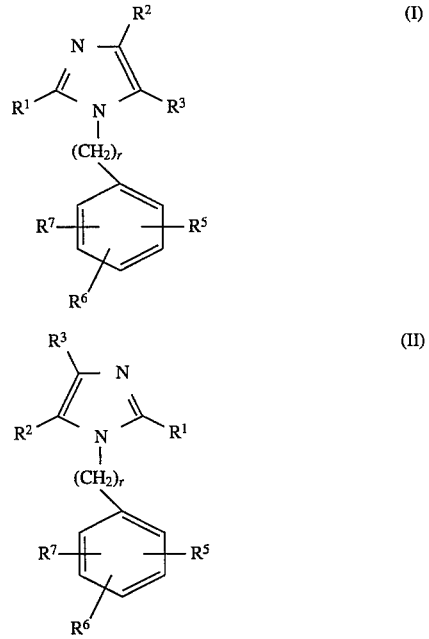

wherein $R^1$ is selected from H; C1–C6 alkyl, C1–C6 fluoroalkyl, C2–C10 alkenyl, or C2–C10 alkynyl; C1–C6 alkyl-CO 2-(C1–C6 alkyl), C1–C6 fluoroalkyl-$CO_2$-(C1–C6 alkyl), C2–C10 alkenyl-CO$_2$-(C1–C6 alkyl), or C2–C10 alkynyl-CO$_2$-(C1–C6 alkyl); C4–C10 cycloalkylalkyl, C3–C6 cycloalkyl, C5–C10 cycloalkylalkenyl, or C5–C10 cycloalkylalkynyl; C4–C10 cycloalkylalkyl substituted by 1–13 —F, C3–C6 cycloalkyl substituted by 1–13 —F, C5–C10 cycloalkylalkenyl substituted by 1–13 —F, or C5–C10 cycloalkylalkynyl substituted by 1–13 —F; C4–C10 cycloalkylalkyl-CO$_2$-(C1–C6 alkyl), C3–C6 cycloalkyl-CO$_2$-(C1–C6 alkyl), C5–C10 cycloalkylalkenyl-CO$_2$-(C1–C6 alkyl), or C5–C10 cycloalkylalkynyl-CO$_2$-(C1–C6 alkyl); phenyl, naphthyl, or aryl-(C1–C4 alkyl); phenyl substituted with —F, naphthyl substituted with —F, or aryl-(C1–C4 alkyl) substituted with —F; phenyl-CO$_2$-(C1–C6 alkyl), naphthyl-CO$_2$-(C1–C6 alkyl), or aryl-(C1–C4 alkyl)-CO$_2$-(C1–C6 alkyl); —(CH$_2$)$_s$O(CH$_2$)$_m$R$^5$; —(CH$_2$)$_s$O(CH$_2$)$_m$R$^5$ substituted with —F; —(CH$_2$)$_s$O(CH$_2$)$_m$R$^5$ substituted with —CO$_2$-(C1–C6 alkyl); benzyl; or benzyl substituted with up to 2 groups selected from halo, C1–C4 alkoxy, NO$_2$, or C1–C4 alkyl;

R$^2$ is C$_1$–C$_6$ alkyl, C$_2$–C$_6$ alkenyl, C$_2$–C$_6$ alkynyl, phenyl-(C$_1$–C$_6$)alkyl, phenyl-(C$_1$–C$_6$)alkenyl, (C$_1$–C$_6$)alkoxy-(C$_1$–C$_6$)alkyl, hydroxy-(C$_1$–C$_6$)alkyl, hydroxy-(C$_2$–C$_6$)alkenyl, hydroxy-(C$_2$–C$_6$)alkynyl, aminocarbonylalkyl, carbonylaminoalkyl, halogen;

R$^3$ is —CN; —CONHR$^1$; or —CO$_2$R$^1$ where R$^1$ as defined above is not H;

R$^5$ is H, Br, I, F, CF$_3$, (C$_1$–C$_4$)alkyl, —C(CF$_3$)$_2$OH, —NHSO$_2$CH$_3$, —C(=O)NHNHSO$_2$CF$_3$,

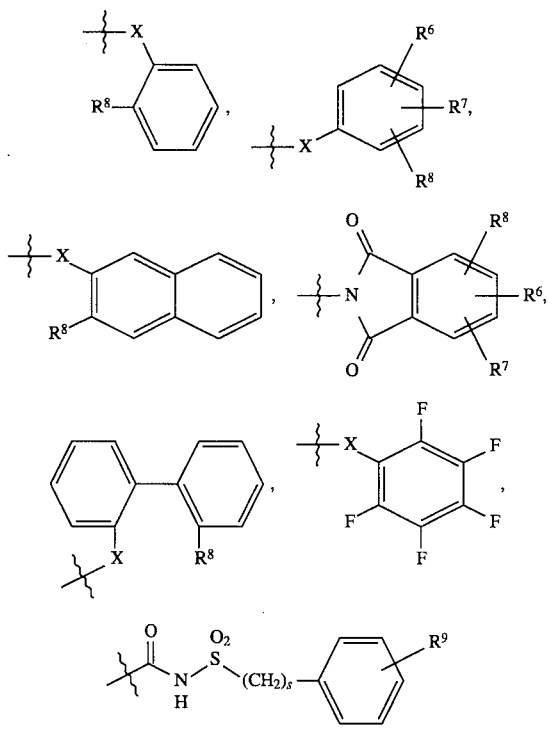

aryl; or aryl substituted by R$^9$;

R$^6$ is H, halo, NO$_2$, C$_1$–C$_4$ alkyl, C$_1$–C$_4$ alkoxy, —NHSO$_2$CH$_3$, —NHSO$_2$CF$_3$, —CONHO—(C$_1$–C$_4$)alkyl, tetrazolyl, trityl tetrazolyl, or furyl;

R$^7$ is H, halo, C$_1$–C$_4$ alkyl, or C$_1$–C$_4$ alkoxy;

X is a single bond, —CO—, —CH$_2$—, —O—, —CONH—, —NHCO—, —OCH$_2$—, —CH$_2$O—, —NHSO$_2$—, —SO$_2$NH—, —CH=CH—, —CF=CH—, —CH=CF—, —CF=CF—, —CH$_2$CH$_2$—, —CF$_2$CF$_2$—, or

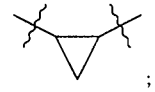

;

R$^8$ is H, —NHSO$_2$CH$_3$, —NHSO$_2$CF$_3$, —NHCOCF$_3$, or —CONHNHSO$_2$CF$_3$;

R$^9$ is H, C$_1$–C$_4$ alkyl, or phenyl;

r is 0 to 2;

m is 1 to 5; and s is 0 to 5;

said method comprising the steps of:

treating a mixture of a compound of formula (I) and its regioisomer of formula (II) in a solvent system, which is:

a) a solvent or mixture of solvents, selected from a halogenated solvent, an ether solvent, a hydrocarbon solvent, a protic solvent, or an aprotic solvent, said solvent or mixture of solvents forming a single liquid phase; or b) a solvent mixture of at least two immiscible solvents, selected from the solvent groups defined in a) above, that results in more than one liquid phase, said solvent mixture additionally containing a phase transfer catalyst present in the range of 1–20% mole based upon the mixture of compounds of formula (I) and formula (II); with 1–20 molar equivalents of an alkali metal hydroxide, and heating the mixture to solvent reflux for a period of time sufficient to preferentially hydrolyze the compound of formula (II) and separating the compound of formula (I) from the hydrolyzed products of compounds of formula (I) and formula (II).

2. The method of claim 1 wherein for the compound of formula (I) and its regioisomer compound of formula (II):

R$^1$ is H, C1–C6 alkyl, C2–C10 alkenyl, or C2–C10 alkynyl;

R$^2$ is C1–C6 alkyl, C2–C6 alkenyl, or C2–C6 alkynyl;

R$^3$ is —CO$_2$R$^1$ where R$^1$ is C1–C6 alkyl, C2–C10 alkenyl, or C2–C10 alkynyl;

R$^5$ is Br, I, F, CF$_3$, —NHSO$_2$CH$_3$, CH$_3$,

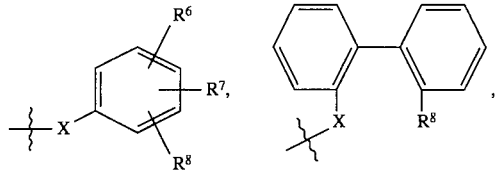

or phenyl, naphthyl, phenyl substituted by R$^9$, or naphthyl substituted by R$^9$;

R$^6$ is independently selected at each occurrence from the group consisting of: H, tetrazolyl, trityl tetrazolyl, or furyl;

and wherein the substituents R$^7$, R$^8$, R$^9$, X, r and m are as defined in claim 1.

3. The method of claim 1 or claim 2 wherein the reaction solvent system is a biphasic solvent system formed of a water immiscible solvent and water.

4. The method of claim 3 wherein the water immiscible solvent is methylene chloride, t-butylmethyl ether, benzene, xylene, toluene, diethyl ether, or hexane.

5. The method of claim 4 wherein the alkali metal hydroxide is sodium hydroxide or potassium hydroxide.

6. The method of claim 5 wherein the phase transfer catalyst is a quaternary ammonium halide or hydroxide.

7. The method of claim 6 wherein the phase transfer catalyst is a tetrabutyl ammonium halide or hydroxide.

8. The method of claim 7 wherein the molar equivalents of an alkali metal hydroxide is in a range of 10–14.

9. The method of claim 8 wherein the molar equivalents of phase transfer catalyst is 10–14% mole based upon the mixture of compounds of the formula (I) and formula (II).

* * * * *